US007321038B2

(12) United States Patent
Wang et al.

(10) Patent No.: US 7,321,038 B2
(45) Date of Patent: *Jan. 22, 2008

(54) METHOD FOR THE CATALYTIC PRODUCTION OF HYDROCODONE AND HYDROMORPHONE

(75) Inventors: Peter Xianqi Wang, Chesterfield, MO (US); Carl Ray White, St. Louis, MO (US)

(73) Assignee: Mallinckrodt Inc., Hazelwood, MO (US)

( * ) Notice: Subject to any disclaimer, the term of this patent is extended or adjusted under 35 U.S.C. 154(b) by 204 days.

This patent is subject to a terminal disclaimer.

(21) Appl. No.: 10/973,031

(22) Filed: Oct. 25, 2004

(65) Prior Publication Data

US 2005/0124811 A1 Jun. 9, 2005

Related U.S. Application Data

(63) Continuation-in-part of application No. 10/495,503, filed on May 13, 2004.

(51) Int. Cl.
*C07D 489/02* (2006.01)
*C07D 489/00* (2006.01)

(52) U.S. Cl. .............................. 546/45; 546/44; 546/46
(58) Field of Classification Search .................. 546/45, 546/44, 46
See application file for complete search history.

(56) References Cited

U.S. PATENT DOCUMENTS

| 2,544,291 A | 3/1951 | Ernst |
| 2,577,947 A | 12/1951 | Baizer et al. |
| 2,628,962 A | 2/1953 | Homeyer et al. |
| 2,649,454 A | 8/1953 | Rapoport |
| 2,654,756 A | 10/1953 | Homeyer et al. |
| 2,715,626 A | 8/1955 | Pfister et al. |
| 4,003,903 A | 1/1977 | Schwartz |
| 4,322,426 A | 3/1982 | Hermann et al. |
| 4,368,326 A | 1/1983 | Rice |
| 4,478,840 A | 10/1984 | Smith, Jr. |
| 4,535,157 A | 8/1985 | Meltzer et al. |
| 4,613,668 A | 9/1986 | Rice |
| 5,571,685 A | 11/1996 | Hailes et al. |
| 5,847,142 A * | 12/1998 | Mudryk et al. ............... 546/45 |
| 6,177,567 B1 | 1/2001 | Chiu et al. |
| 6,235,906 B1 | 5/2001 | Sebastian |
| 2001/0005754 A1 | 6/2001 | Chiu et al. |
| 2001/0018519 A1 | 8/2001 | Sebastian |

FOREIGN PATENT DOCUMENTS

| DE | 365683 | 12/1922 |
| DE | 415097 | 6/1925 |
| DE | 607931 | 1/1935 |
| DE | 617238 | 10/1935 |
| DE | 623821 | 1/1936 |

| WO | PCT/GB97/01977 | 2/1998 |
| WO | WO 01/34608 | 5/2001 |

OTHER PUBLICATIONS

William S. Knowles, K. Ryoji Noyori, and Barry Sharpless; Information for the Public, the 2001 Nobel Prize in Chemistry: Mirror Image Catalysis; *Kungl Vetenskapsakademien, The Royal Swedish Academy of Sciences*; Apr. 8, 2002.
Bernard Demerseman, Ronan Le Lagadec, Benedicte Guilbert, Corinne Renouard, Pascale Crochet, and Pierre H. Dixneuf; Chelating and Hemilabile Properties of β- and γ-Keto Phosphines: (n⁶-Arene) ruthenium (II) Derivatives from γ-Keto Phosphines and synthesis and Reactivity of Bis (n²-keto phosphine-P,O) ruthenium (II) Complexes; *Advance ACS Abstracts*, Organometallics Vo. 13, No. 6, May 1, 1994.
Manuel M. Baizer, Kurt S. Ellner, and Athanasios Loter; The Rearrangement of Codeine to Dihydrocodeinone; *Journal of the American Pharmaceutical Association*, vol. XL, p. 580-582; Nov. 1951.
Annika Rimland, Goran Bergson, Ulf Obenius, Stefan Sjoberg, and Bengt Langstrom; Synthesis of N-[Methyl-$^{11}$C] Hydromorphone by Using Multivariate Strategies for Optimization of Radiochemical Yields; Appl. Radiat. Isol., vol. 38, No. 8, p. 651-654; 1987.
Katada, Masa; Yakugaku Zasshi, Morphine bases. III. Conversion of Phenylpseudocodeine, *Journal of the Pharmaceutical Society of Japan*; vol. 62, p. 347-355; Nippon Yakugakkai, Japan, 1942. This Article is relevant since it discloses that codeine was arranged to dihydrocodeinone in 50-79% yields using 10% Palladium black as catalyst, 6% Hydrochloric acid as medium, a temperature of 50-80oC and a current of hydrogen. But the reference is not involved in our claims on isomerization of codeine and morphine by a transition metal complex of a tertiary phosphine halid, $[M(PR_3)_nX_m]_p$. (Abstract is provided in English).
Nippon Yakugakkai; Electrolytic Reduction of Morphine and Codine; *Journal of the Pharmaceutical Society of Japan*; vol. 56, pp. 44-52; Nippon Yakugakkai, Japan, 1936.This Article is relevant since it discloses electronic reduction of codeine and morphine to dihydrocodeine and dihydromorphine, respectively. But the reference is not involved in our claims on isomerization of codeine and morphine by a transition metal complex of a tertiary phosphine halid, $[M(PR_3)_nX_m]_p$. (Abstract is provided in English).
C. Mannich and H. Lowenheim; Archiv der Pharmazie; *Arch. Pharm.*; vol. 258, p. 295-316; 1920. This Article is relevant since it discloses reduction of codeinnone to dihydrocodeinone in the presence of Pd and hydrogen. But the reference is not involved in our claims on isomerization of codeine and morphine by a transition metal complex of a tertiary phosphine halid, [M(PR3)nXm]p. (Abstract is provided in English).
PCT International Search Report dated Jul. 12, 2004; International Application No. PCT/US03/35462; Applicant: Mallinckrodt, Inc.; International Filing Date Nov. 5, 2003.

(Continued)

*Primary Examiner*—Charanjit S. Aulakh
(74) *Attorney, Agent, or Firm*—Sarah Pfeifer Vaz; Blackwell Sanders LLP

(57) ABSTRACT

A method for the catalytic conversion of codeine, morphine or analogs thereof into hydrocodone, hydromorphone or analogs thereof utilizing a transition metal catalyst of the formula $[M(PR^3R^4R^5)_nX_m]_p$; wherein $R^1$ is H, alkyl, aryl or acyl; M is a Group VIII transition metal; $R^3$, $R^4$ and $R^5$ are selected from the group consisting of alkyl, aryl, alkoxyl, phenoxyl and combinations thereof; X is a halide or an anion; n is 1, 2, 3 or 4; m is 1 or 2; and p is at least 1.

32 Claims, No Drawings

OTHER PUBLICATIONS

Ninan, Aleyamma and Sainsbury, Malcolm (School of Chemistry, University of Bath, Claverton Down, Bath BA2 7AY, UK); An Improved Synthesis of Noroxymorphone; *Tetrahedron*, vol. 48, No. 32, pp. 6709-7616 (1992) (printed in Great Britain).

Rapoport, Henry; Naumann, Robert; Bissell, Eugene; and Bonner, Robert. *The Preparation of some Dihydro Ketones in the Morphine Series by Oppenauer Oxidation*; Oppenauer Oxidation in Morphine Series, pp. 1103-1107, Chemical Laboratory of the University of California, May 12, 1950, (Printed in Berkeley, California U.S.A.).

S.G. Davies et al.; Synthesis of 10(s)-Methyl-codeine & 20(s)-methyl-morphine; J. Chimie, 1980, p. 369-375.

Nathan L. Smith, Synthesis of Phenothiazine Derivatives for Use As Antioxidants, J. Org. Chem., 1950, 15, p. 1130.

J. Am. Pharm. Assoc., 1950, 40, p. 480.

S.G. Davies et al.; Palladium Catalyzed elaboration of Codeine & Morphine; J. Chem. Soc., Perkin Trans., 2001, 1, (12), p. 1413-1420.

\* cited by examiner

METHOD FOR THE CATALYTIC PRODUCTION OF HYDROCODONE AND HYDROMORPHONE

CROSS REFERENCE TO RELATED APPLICATIONS

This application is a continuation-in-part of application Ser. No. 10/495,503, filed May 13, 2004, said application claims priority to provisional application 60/425,360 filed Nov. 11, 2002, are both hereby incorporated by reference in their entirety.

BACKGROUND OF THE INVENTION

The present invention relates to a method for the catalytic production of hydrocodone, hydromorphone, and analogs thereof, and more particularly to a method for catalytically converting codeine and morphine into hydrocodone and hydromorphone, respectively.

Hydrocodone and hydromorphone are opioid analgesics having similar qualities to codeine and morphine. Conventional methods for producing hydrocodone and hydromorphone typically involve a two step oxidation/reduction route from codeine and morphine. Unfortunately, these methods are expensive and inefficient. Attempts to improve efficiency have included the use of catalytic methods. Known methods include the use of metallics, typically Ru, Rh, Pd and Pt on activated carbon as well as metallic complexes. The preparation of these catalysts is difficult, yields are poor, and isolation of the product is often burdensome.

Other catalytic methods, including the use of finely-divided platinum or palladium in an acidic media, are environmentally undesirable. Enzymatic methods of conversion have also been attempted, but as with the methods of catalysis discussed above, these methods are costly and difficult to scale up.

There is therefore a need for an improved method of conversion that is easily scaled up and economical for manufacturing purposes.

SUMMARY OF THE INVENTION

An aspect of the present invention is to provide a method for the catalytic conversion of a compound of Formula I into a compound of Formula II utilizing at least one transition metal complex as catalyst,

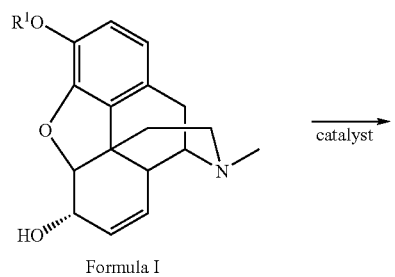

Formula I

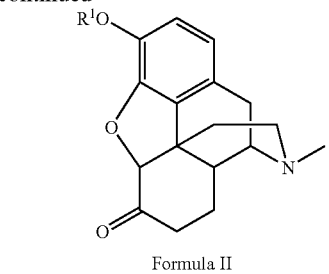

Formula II wherein $R_1$ is H, alkyl, aryl or acyl.

In one aspect of the present invention the transition metal complex is of the formula $[M(PR^3R^4R^5)_nX_m]_p$; wherein M is a Group VIII transition metal; $R^3$, $R^4$ and $R^5$ are selected from the group consisting of alkyl, aryl, alkoxyl, phenoxyl and combinations thereof; X is a halide or an anion; n is 1, 2, 3 or 4; m is 1 or 2; and p is at least 1.

Another aspect of the present invention is to provide a one step method for the conversion of codeine or morphine into hydrocodone or hydromorphone, respectively.

These are merely illustrative aspects of the present invention and should not be deemed an all-inclusive listing of the innumerable aspects associated with the present invention. These and other aspects will become apparent to those skilled in the art in light of the following disclosure.

DETAILED DESCRIPTION

There is provided a method for the conversion of a compound according to Formula I to a compound according to Formula II,

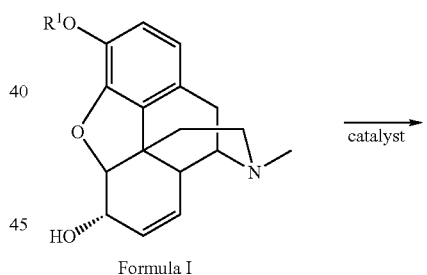

Formula I

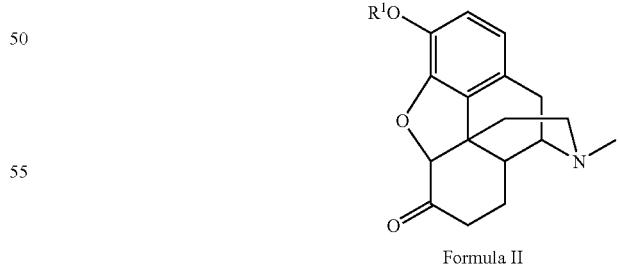

Formula II wherein $R^1$ is H, alkyl, aryl or acyl.

The method of the present invention is especially useful where $R^1$ is methyl or H, i.e., codeine or morphine, respectfully, leading to the formation of hydrocodone or hydromorphone, respectfully.

In one embodiment of the present invention, the transition metal catalysts of the present invention comprise a transition metal complex $[M(PR^3R^4R^5)_nX_m]_p$, wherein M is preferably a Group VIII transition metal; $R^3$, $R^4$ and $R^5$ are independently selected from alkyl, aryl, and alkoxyl, phenoxyl groups; X is a halide or an anion; n is 1, 2, 3 or 4; and m is 1 or 2. These complexes are capable of polymerizing, therefore p is at least 1. When all three of the R groups are alkoxyl, phenoxyl or combinations thereof, the ligand of the complex is termed a tertiary phosphite. If at least one of the R groups is not an alkoxyl or phenoxyl, then the ligand of the complex is termed a tertiary phosphine. Preferred metals include Rh, Ru, Pd and Pt. The halide, X, is typically Cl or Br. Anions include but are not limited to $BF_4$, $PF_6$, $ClO_4$, $CHO_2$, $CF_3CO_2$, $CF_3SO_3$, $CH_3CO_2$, $ArCO_2$, $CH_3SO_3$, p-tolylSO$_3$, HSO4 and $H_2PO_4$. $R^2$ is an alkyl or aryl group, with phenyl being preferred. Many of these catalysts are commercially available, or are easily prepared as is known in the art.

In another embodiment of the present invention, the transition metal catalysts of the present invention comprise a transition metal complex of a tertiary phosphine halide, $[M(PR^2_3)_nX_m]_p$, wherein M is preferably a Group VIII transition metal; $R^2$ is an alkyl or aryl; X is a halide or an anion; n is 1, 2, 3 or 4; and m is 1 or 2. These complexes are capable of polymerizing, therefore p is at least 1. Preferred metals include Rh, Ru, Pd and Pt. The halide, X, is typically Cl or Br. Anions include but are not limited to $BF_4$, $PF_6$, $ClO_4$, $CHO_2$, $CF_3CO_2$, $CF_3SO_3$, $CH_3CO_2$, $ArCO_2$, $CH_3SO_3$, p-tolylSO$_3$, $HSO_4$ and $H_2PO_4$. $R^2$ is an alkyl of aryl group, with phenyl being preferred. Many of these catalysts are commercially available, or are easily prepared as is known in the art. It is noted that the catalysts of the formula $[M(PR_{23})_nX_m]_p$ are a subgroup of the broader group of catalysts $[M(PR^3R^4R^5)_nX_m]_p$.

The complexes of the present invention may be comprised of solid supported tertiary phosphines/phosphites, including but not limited to polymer supported tertiary phosphines/phosphites, silical supported tertiary phosphines/phosphites and resin-bound tertiary phosphines/phosphites. In the case of solid supported tertiary phosphines/phosphites, one of the R groups typically contains a linking group connecting a phosphine/phosphite and a solid phase, as is well known in the art. A non-limiting example of a solid supported tertiary phosphine useful in the present invention is the copolymer prepared from the monomer p-styryldiphenylphosphine also known as diphenyl(p-vinylphenyl)phosphine with styrene or silical supported tertiary phosphines made from treating silica with $(EtO)_3SiCH_2CH_2PPh_2$. There are solid supported tertiary phosphines/phosphites that are commercially available.

In Formula I and Formula II, alkyl groups useful therein typically include those having from about 1 to about 10 carbon atoms. Aryl groups in Formula I and Formula II include phenyl and substituted phenyl groups.

In one embodiment of the invention the metal is Rh and the complex is of the formula $[Rh(PR^3R^4R^5)_nX_m]_p$; wherein $R^3$, $R^4$ and $R^5$ are selected from the group consisting of alkyl, aryl, alkoxyl, phenoxyl and combinations thereof; X is a halide or an anion; n is 1, 2, 3 or 4; m is 1 or 2; and p is at least 1.

In another embodiment of the present invention the transition metal is Rh, and the metal complex is of the formula $[Rh(PR^2_3)_nY]_p$, wherein $R^2$ is an alkyl or aryl, X is a halide, n is 1, 2 or 3, and p is at least 1, or of the formula $[Rh(PR^2_3)_nY]_p$, wherein $R^2$ is an alkyl or aryl, n is 1, 2 or 3, p is at least 1 and Y is an anion, preferably including $BF_4$, $PF_6$, $ClO_4$, $CHO_2$, $CF_3CO_2$, $CF_3SO_3$, $CH_3CO_2$, $ArCO_2$, $CH_3SO_3$, p-tolylSO$_3$, $HSO_4$ or $H_2PO_4$.

In yet another embodiment of the present invention the transition metal is Ru and the metal complex is of the formula $[Ru(PR^3R^4R^5)_nX_m]_p$; wherein $R^3$, $R^4$ and $R^5$ are selected from the group consisting of alkyl, aryl, alkoxyl, phenoxyl and combinations thereof; X is a halide or an anion; n is 1, 2, 3 or 4; m is 1 or 2; and p is at least 1.

In another embodiment the transition metal is Ru and the metal complex is of the formula $[RuX_2(PR^2_3)_n]_p$ wherein $R^2$ is an alkyl or aryl, X is a halide, n is 1, 2, 3 or 4; and p is at least 1 or of the formula $[RuYX(PR^2_3)_n]_p$ wherein $R^2$ is an alkyl or aryl and wherein n=3, p is at least 1, Y=H and X=Cl; n=3, Y=H and X=H; n=4, X=H, Y=H; or n=2, 3 or 4, p is at least 1 and X=Y=$ClO_4$, $CF_3SO_3$, $PF_6$ or $BF_4$, $CHO_2$, $CH_3CO_2$, $ArCO_2$, $CH_3SO_3$, p-tolylSO$_3$, $HSO_4$ or $H_2PO_4$.

A suitable method for producing an illustrative Ru complex of the present invention involves refluxing a Ru salt, for example $RuCl_3 \cdot xH_2O$ with an excess of triphenylphosphine in alcohol to form the complex $[Ru(P(C_6H_5)_3)_3Cl_2]_p$.

An illustrative Rh complex of the present invention is also commercially available, or can be prepared by refluxing rhodium trichloride with triphenylphosphine in alcohol, typically methanol or ethanol.

In another illustrative embodiment of the present invention the Rh—, Ru—, and/or Ir— complex can be bound to a tertiary copolymer of styrene, divinylbenzene, and diphenyl(p-vinylphenyl)phosphine also known as p-styryldiphenylphosphine, illustrated in Formula III:

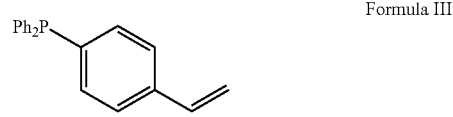

Formula III

Optionally, other monomers may be substituted or added to optimize certain physical properties of the overall polymeric catalyst. Illustrative examples include but are not limited to, ethylene dimethacrylate, p-bromostyrene, and crosslinking agents such as divinylbenzene, butadiene, diallyl maleate, diallyl phthalate, glycol dimethacrylate, and other di- or triolefins. Other phosphine containing monomers bound to the styrene ring can have, in addition to diaryl substitutions, dialkyl, branched and cyclic dialkyl, dialkoxyl or mixed substitutions or these. Illustrative examples utilizing styrene are shown in Formulas IV and V.

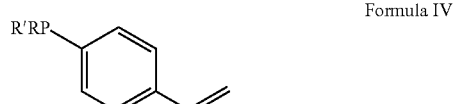

Formula IV

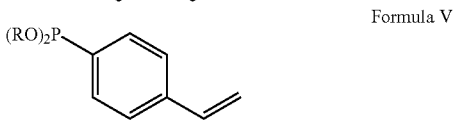

Formula V

The polymeric complex makes up a composition of matter consisting essentially of an intrinsically porous solid organic styrene-divinyl benzene copolymer; a substituent phosphine group chemically bonded through phosphorus to a carbon atom of said polymer; and a Group VIII metal chemically bonded to said substituent phosphine which composition is substantially insoluble in the solvent(s).

In an illustrative embodiment the polymeric support is composed of a styrene divinylbenzene copolymer containing 2 to 20 mole percent divinylbenzene, in which 0.5 to 7 mole percent, preferably 5 to 6 mole percent of the pendant phenyl groups from the copolymerized styrene contain the diphenylphosphine moiety at the para position. The composition of the polymer support is 75 to 97.6 mole percent styrene, 2 to 20 percent divinylbenzene and 0.4 to 6 percent p-diphenylphosphenostyrene.

As to the amount of ruthenium complex in the catalyst, typically the Ru/pendant atom ratio is preferably at least 0.001 and is more preferably about 0.5 to an upper limit set by the point at which the polymer support will no longer take up complex, for example about 1.2.

The polymeric complex may be made by contacting a solution of the Group VIII metal salt complex in solution with the polymer support. For practical application, the metal complex is dissolved in a suitable solvent including but not limited to water, methanol, ethanol, isopropanol, isobutyl alcohol, N-methylpyrrolidone, N,N-dimethylformamide, N,N-dimethylacetamide and mixtures thereof. The Group VIII metal complex solution should be at least $10^{-6}$ M in the ruthenium complex but is preferably about $10^{-3}$ M in the ruthenium complex.

In this illustrative embodiment, the polymer portion of the catalyst is intrinsically porous. Porosity of the polymer portion of the catalyst imparts increased activity to the catalyst. With catalysts having an organic polymer portion which is not intrinsically porous, porosity may be induced into the polymer portion by solvent swelling. Combinations of the above-noted solvents can be manipulated to produce various degrees of swelling of the polymer portion of the catalyst, as is well known in the art.

The catalytic conversion of the present invention has the further economic advantage of being able to convert a salt of codeine or morphine, for example codeine hydrochloride or morphine hydrochloride, to hydrocodone or hydromorphone, respectively.

Further, the catalysts of the present invention facilitate high value metal recovery of the metal containing solid catalyst. When recovered by conventional methods known in the art, the metal of the present catalyst results in an improved recovery percentage. This further reduces material and labor costs, as well as simplifying processing/workup. For purposes herein, the term recovery is meant to encompass recovery, recycling and/or regeneration of the metal.

In the embodiments wherein the catalyst is on a fixed support, the catalyst/support can be placed in a column or container as part of a loop reactor. In a non-limiting illustrative example codeine in alcohol that is heated in a reactor can be pumped or gravity fed through a catalyst bed and cycled back to the reactor until the desired conversion to hydrocodone is produced. The advantages of this method include that many cycles (perhaps several batches) of product may be obtained with a given bed. The catalyst value is then easily recovered and sent back for reprocessing. The purification workup is simplified because the catalyst is not present in the solution. For practical reasons, the concentration of Group VIII metals must be below about 10 ppm in the product. On cooling, the product would crystallize out of solution in high purity, to be recovered by filtration or centrifugation.

Many process designs, as are well known in the art, could be utilized with the process of the present invention.

The reaction of the present invention may be accomplished by any conventional process. A suitable process includes dissolving the reactant of Formula I in a suitable solvent in a reaction vessel. Suitable solvents include but are not limited to alcohols, preferably primary and secondary lower alkyl alcohols. The reaction vessel is then flushed with an inert atmosphere, typically nitrogen. The catalyst is added and the reaction mixture is refluxed under the inert atmosphere until the conversion is essentially complete, typically at least about an hour. The reaction mixture is cooled and crystals of the product are collected. The product may be purified by recrystallization in a suitable solvent as is well known in the art, or by any other suitable conventional method of purification.

In an alternative embodiment a tertiary amine, for example triethylamine, is added to the reaction mixture when the preferred Ru complex catalyst is used. The tertiary amine reduces the formation of side products, primarily the alkaloid neopine, a potential side product in reactions of the present invention utilizing the preferred Ru catalyst.

In another alternative embodiment the alkaloid compound is added to the reactants that form the catalyst and the catalyst formation reaction takes place in the presence of the alkaloid. The ability to form the catalyst and subsequently accomplish the catalytic conversion in the same reaction vessel further enhances the economy of the reaction.

EXAMPLES

Example 1

Codeine, 50.00 g, was dissolved in 200 ml methanol in a three-neck flask at room temperature. The flask was equipped with a condenser and nitrogen. The flask was flushed with nitrogen for five minutes with one neck opened. The catalyst, 0.50 g of $RhCl(P(C_6H_5)_3)_3$ was added to the solution. The flask was then flushed with nitrogen for another five minutes, and the open neck was closed. The reaction mixture was stirred under nitrogen and heated to reflux for four hours, then cooled to 0° C. for 30 minutes. The resulting crystals were removed by filtration. The collected crystals were washed four times with 10 ml cold methanol (5° C.), and dried in air for one hour yielding pale yellow crystals (41.50 g, yield 83%). The filtrate was pumped down to dryness to give 6.14 g yellow solid. The solid residue was dissolved in 40 ml refluxing methanol and cooled to 0° C. for 30 minutes and filtered. The collected crystals were washed four times with 3 ml portions of cold methanol (5° C.) and air dried for 2 hours yielding 3.41 g (6.8%) white crystals. HPLC analysis and NMR spectra confirm that the product is pure hydrocodone.

Example 2

Morphine, 50.00 g, was suspended in 500 ml methanol in a three neck flask equipped with condenser and nitrogen input and outlet. After refluxing under nitrogen for five minutes, one neck of the flask was opened. A catalyst, 0.50 g $RhCl(P(C_6H_5)_3)_3$-was added to the container. The opened neck was closed with a stopper. The reaction mixture was stirred under nitrogen and heated to reflux for 6 hours, cooled down to 0° C. for 30 minutes, and filtered. The collected solid was washed four times with cold methanol (5° C.) and dried in air for 20 minutes. The solid was kept under vacuum (15 mm Hg) at room temperature for 1 hour, yielding a white powder (38.83 g, yield 77.7%). The filtrate was distilled under nitrogen until only 200 ml of solution remained. It was cooled down to 0° C. for 30 minutes and filtered, yielding a white powder. The product was washed twice with 20 ml each and then once with 10 ml of cold methanol (5° C.) dried in air for 40 minutes to yield 3.48 g of a white powder product. HPLC analysis and NMR spectra confirm product is pure hydromorphone.

Example 3

Ruthenium dimer was prepared by refluxing 1 g RuCl$_3$xH$_2$O with 3 equivalents P(C$_6$H$_5$)$_3$ in EtOH (100 ml) overnight. The resulting catalyst, [Ru(P(C$_6$H$_5$)$_3$)$_2$Cl$_2$]$_2$ was obtained as a black precipitate after filtration, 63% yield.

Example 4

The catalyst of Example 3 was reacted with codeine in MeOH in the presence of triethylamine in the ratios shown in the table below. The reaction mixtures were flushed with N$_2$ for 5 minutes, heated to reflux under N$_2$, cooled to 0° C. and filtered. The recovered crystals were washed twice with 5 ml MeOH and air dried to yield white crystals.

TABLE 1

| Starting Materials | [Ru(P(C$_6$H$_5$)$_3$)$_2$Cl$_2$]$_2$ | MeOH | NEt$_3$ | Reaction time | Products | Hydrocodone/ codeine/neopine (area % by HPLC) |
|---|---|---|---|---|---|---|
| Codeine 1.0 g | 10 mg | 5 ml | 0.25 ml | 2 h | 0.85 g | 96.7/1.8/0.33 |
| Codeine 1.0 g | 10 mg | 5 ml | 0.25 ml | 3 h | 0.99 g | 94.7/0/0 |
| Codeine 2.5 g | 25 mg | 12.5 ml | 0.725 ml | 3 h | 1.58 g | 100/0/0 |
| Codeine 1 g/Codeine. sulfate 0.05 g | 10 mg | 5 ml | 0.25 ml | 3 h | 0.61 g | 97.4/1.0/0 |
| Codeine 1 g/ CodeineHCL 0.05 g | 55 mg | 10 ml | 0 | 3 h | 1.17 g | 77.5/2.5/0.8 |
| CodeineHCl 1.1 g | 100 mg | 10 ml | 0 | 15 h | 1.16 g | 81.5/11.6/0 |
| Morphine (recry) 1.0 g | 80 mg | 10 ml | 0.25 | 3 days | 1.08 g | Hydromorphone/ morphine = 88.6/6.1 |

Example 5

Codeine, 5.0 g, and 0.117 g catalyst, Ru(P(C$_6$H$_5$)$_3$)$_3$Cl$_2$, were dissolved in 25 ml EtOH. The mixture was flushed with nitrogen for 5 minutes. After refluxing under nitrogen for 2 hours the reaction mixture was cooled down to 0° C. and filtered. The collected crystals were washed twice with 5 ml each MeOH and dried in air for 1 hour to yield white crystals, 70% yield hydrocodone.

Example 6

Morphine, 1.0 g, and 80 mg [Ru(P(C$_6$H$_5$)$_3$)$_2$Cl$_2$]$_2$ was suspended in 10 ml MeOH. The reaction mixture was flushed with N$_2$ for 3 minutes, after which 0.25 ml triethylamine was added, and the mixture flushed with N$_2$ for another 3 minutes. The reaction mixture was heated to reflux with stirring under N$_2$ for 72 hours. The resulting solid was found to be hydromorphone.

Example 7

Codeine, 5.09 g, 25.4 mg RuCl$_3$xH$_2$O and 95.9 mg P(C$_6$H$_5$)$_3$ were added to 25 ml ethanol in a three neck flask. The flask was flushed with N$_2$ for 5 minutes. The mixture was heated until reactants dissolved, and then refluxed, under nitrogen, overnight. The resulting solution was washed twice with 5 ml each MeOH and air dried to yield 3.31 g product. Analysis determined the presence of hydrocodone and Ru catalyst.

Example 8

Codeine-HCl, 1.1 g and 0.1 g RuCl$_2$(P(C$_6$H$_5$)$_3$)$_3$ were stirred in 10 ml MeOH and flushed with N$_2$ for 5 minutes. The reaction mixture was refluxed overnight under N$_2$, cooled to room temperature and dried under vacuum, yielding 1.16 g brown solid containing hydrocodone.

Example 9

Ru Polymer Catalyst Conversion to Hydrocodone:
Codeine, 50.00 g, is added to 200 ml methanol contained in a three necked flask equipped with condenser and nitrogen input and outlet. The mixture is taken to reflux under nitrogen. A polymer phosphine anchored Ru catalyst, 5 g (1 mole % Ru) is added to the container. The reaction mixture is stirred under nitrogen at reflux for several hours. An additional 800 ml of methanol is added and heating is continued for 30 minutes. The polymer catalyst is recovered for recycle by filtration of the hot liquor. About 800 ml of methanol is removed from the filtrate by distillation. The liquor is then cooled to 0° C. and maintained at that temperature for at least about 30 minutes. The product is collected by filtration, washed four times with cold methanol (5° C.) and air dried. The product is placed under vacuum (<15 mm Hg) at room temperature for at least an hour. The product is obtained as a white powder weighing over 38 grams for a >75% yield. The purity and identity of the hydrocodone is confirmed by HPLC, H$^1$ and C$^{13}$ NMR and MS analyses.

From the foregoing description those skilled in the art will appreciate that economical and efficient methods for the catalytic conversion of codeine or morphine into hydrocodone or hydromorphone, respectively, are provided.

Having described the invention in detail, those skilled in the art will appreciate that modifications may be made of the invention without departing from its spirit and scope. Therefore, it is not intended that the scope of the invention be limited to the specific embodiments described. Rather, it is intended that the appended claims and their equivalents determine the scope of the invention.

The invention claimed is:

1. A method comprising catalytically converting a compound of Formula I into a compound of Formula II utilizing at least one transition metal complex of the formula $[M(PR^3R^4R^5)_nX_m]_p$; wherein $R^1$ is H, alkyl, aryl or acyl; M is a Group VIII transition metal; $R^3$, $R^4$ and $R^5$ are selected from the group consisting of alkyl, aryl, alkoxyl, phenoxyl and combinations thereof; X is H, a halide or an anion; n is 1, 2, 3 or 4; m is 1 or 2; and p is at least 1.

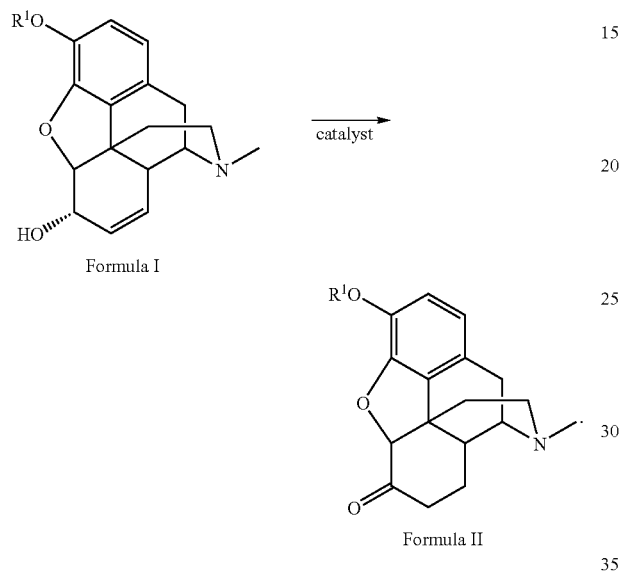

2. The method of claim 1 wherein $R^1$ is H or CH3.

3. The method of claim 1 wherein $(PR^3R^4R^5)_n$ is supported by a solid.

4. The method of claim 1 wherein $(PR^3R^4R^5)_n$ is selected from the group consisting of polymer supported $(PR^3R^4R^5)_n$, silical supported $(PR^3R^4R^5)_n$, resin-bound $(PR^3R^4R^5)_n$ and mixtures thereof.

5. The method of claim 1 wherein the metal complex is bound to a tertiary copolymer selected from the group consisting of styrene, divinylbenzene, and diphenyl(p-vinylphenyl)phosphine.

6. The method of claim 5 wherein the copolymer is substituted with a monomer selected from the group consisting of ethylene dimethacrylate, p-bromostyrene, divinylbenzene, butadiene, diallyl maleate, diallyl phthalate, glycol dimethacrylate, diolefins and triolefins.

7. The method of claim 1 wherein the metal complex is of the formula $[Rh(PR^3R^4R^5)_nX_m]_p$; $R^3$, $R^4$ and $R^5$ are selected from the group consisting of alkyl, aryl, alkoxyl, phenoxyl, and combinations thereof; X is a halide or an anion; n is 1, 2, 3 or 4; m is 1 or 2; and p is at least 1.

8. The method of claim 7 wherein n is 1, 2 or 3; p is at least 1; and X is selected from the group consisting of $BF_4$, $PF_6$, $ClO_4$, $CHO_2$, $CF_3CO_2$, $CF_3SO_3$, $CH_3CO_2$, $ArCO_2$, $CH_3SO_3$, p-tolylSO_3$, $HSO_4$ and $H_2PO_4$.

9. The method of claim 1 wherein in the metal complex is of the formula $[RuXY(PR^3R^4R^5)_n]_p$; $R^3$, $R^4$ and $R^5$ are selected from the group consisting of alkyl, aryl, alkoxyl, phenoxyl and combinations thereof; X is an H, halide or an anion; Y is an H, halide or an anion; n is 1, 2, 3 or 4; m is 1 or 2; and p is at least 1.

10. The method of claim 9 wherein n=3, p is at least 1, Y=H and X=Cl; or n=3, p is at least 1, Y=H and X=H; or n=4, p is at least 1, X=H, Y=H; or n=2, 3 or 4 and X=Y is selected from the group consisting of $ClO_4$, $PF_6$, $BF_4$, $CHO_2$, $CF_3CO_2$, $CF_3SO_3$, $CH_3CO_2$, $ArCO_2$, $CH_3SO_3$, p-tolylSO_3$, $HSO4$ and $H_2PO_4$.

11. A method comprising catalytically converting a compound of Formula I into a compound of Formula II utilizing at least one transition metal complex of a tertiary phosphine halide, wherein $R^1$ is H, alkyl, aryl or acyl; the metal complex is of the formula $[M(PR^2{}_3)_nX_m]_p$ wherein M is a Group VIII transition metal; $R^2$ is an alkyl or aryl; X is H, a halide or an anion; n is 1, 2, 3 or 4; p is at least 1; and m is 1 or 2

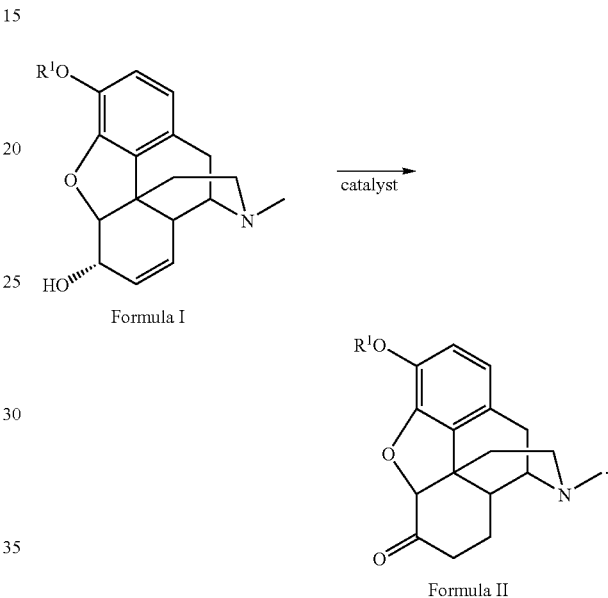

12. The method of claim 11 wherein $R^1$ is H or CH$_3$.

13. The method of claim 11 wherein the metal complex is of the formula $[Rh(PR^2{}_3)_nX]_p$, wherein $R^2$ is an alkyl or aryl; X is a halide or an anion; n is 1, 2 or 3; and p is at least 1.

14. The method of claim 13 wherein the metal complex is of the formula $[Rh(PR^2{}_3)_nY]_p$, wherein n is 1, 2 or 3; p is at least 1; and Y is selected from the group consisting of $BF_4$, $PF_6$, $ClO_4$, $CHO_2$, $CF_3CO_2$, $CF_3SO_3$, $CH3CO_2$, $ArCO_2$, $CH_3SO_3$, p-tolylSO_3$, $HSO4$ and $H_2PO_4$.

15. The method of claim 11 wherein in the metal complex is of the formula $[RuX_2(PR^2{}_3)_n]_p$ wherein $R^2$ is an alkyl or aryl; X is a halide; n is 1, 2, 3 or 4; and p is at least 1.

16. The method of claim 11 wherein the metal complex is of the formula $[RuYX(PR^2{}_3)_n]_p$ wherein $R^2$ is an alkyl or aryl and wherein n=3, p is at least 1, Y=H and X=Cl; or n=3, p is at least 1, Y=H and X=H; or n=4, p is at least 1, X=H, Y=H; or n=2, 3 or 4 and X=Y is selected from the group consisting of $ClO_4$, $CHO_2$, $PF_6$, $BF_4$. $CHO_2$, $CF_3CO_2$, $CF_3SO_3$, $CH_3CO_2$, $ArCO_2$, $CH_3SO_3$, p-tolylSO_3$, $HSO_4$ and $H_2PO_4$.

17. A method for producing hydrocodone comprising converting codeine into hydrocodone in the presence of at least one transition metal complex of the formula $[M(PR^3R^4R^5)_nX_m]_p$; wherein M is a Group VIII transition metal; $R^3$, $R^4$ and $R^5$ are selected from the group consisting of alkyl, aryl, alkoxyl, phenoxyl and combinations thereof; X is H, a halide or an anion; n is 1, 2, 3 or 4; m is 1 or 2; and p is at least 1.

18. The method of claim 17 wherein $(PR^3R^4R^5)_n$ is supported by a solid.

19. The method of claim 17 wherein $(PR^3R^4R^5)_n$ is selected from the group consisting of polymer supported $(PR^3R^4R^5)_n$, silical supported $(PR^3R^4R^5)_n$, resin-bound $(PR^3R^4R^5)_n$ and mixtures thereof.

20. The method of claim 17 wherein the metal complex is of the formula $[Rh(PR^2{}_3)_nX]_p$, wherein $R^2$ is an alkyl or aryl; X is a halide or an anion; n is 1, 2 or 3; and p is at least 1.

21. The method of claim 17 wherein the metal complex is of the formula $[Rh(PR^2{}_3)_nY]_p$, wherein $R^2$ is an alkyl or aryl; n is 1, 2 or 3; p is at least 1; and Y is selected from the group consisting of $BF_4$, $PF_6$, $ClO_4$, $CHO_2$, $CF_3CO_2$, $CF_3SO_3$, $CH_3CO_2$, $ArCO_2$, $CH_3SO_3$, p-tolyl$SO_3$, HSO4 and $H_2PO_4$.

22. The method of claim 17 wherein in the metal complex is of the formula $[RuX_2(PR^2{}_3)_n]_p$ wherein $R^2$ is an alkyl or aryl; X is a halide; n is 1, 2, 3 or 4; and p is at least 1.

23. The method of claim 17 wherein the metal complex is of the formula $[RuYX(PR^2{}_3)_n]_p$ wherein $R^2$ is an alkyl or aryl and wherein n=3, p is at least 1, Y=H and X=Cl; or n=3, p is at least 1, Y=H and X=H; or n4, X=H, Y=H; or n=2, 3 or 4, p is at least 1 and X=Y is selected from the group consisting of $ClO_4$, $CHO_2$, $PF_6$, $BF_4$, $CHO_2$, $CF_3CO_2$, $CF_3SO_3$ $CH_3CO_2$, $ArCO_2$, $CH_3SO_3$, p-tolyl$SO_3$, HSO4 and $H_2PO_4$.

24. A method for producing hydromorphone comprising converting morphine into hydromorphone in the presence of at least one transition metal complex of a tertiary phosphine wherein the metal complex is of the formula $[M(PR^2{}_3)_nX_m]_p$ wherein M is a Group VIII -transition metal, $R^2$ is an alkyl or aryl; X is H, a halide or an anion; n is 1, 2, 3 or 4; p is at least 1; and m is 1 or 2.

25. The method of claim 24 wherein the metal complex is of the formula $[Rh(PR^2{}_3)_nX]_p$, wherein $R^2$ is an alkyl or aryl; X is a halide or an anion; n is 1, 2 or 3; and p is at least 1.

26. The method of claim 24 wherein the metal complex is of the formula $[Rh(PR^2{}_3)_nY]_p$, wherein $R^2$ is an alkyl or aryl; n is 1, 2 or 3; p is at least 1; and Y is selected from the group consisting of $BF_4$, $PF_6$, $ClO_4$ $CF_3CO_2$, $CF_3SO_3$, $CH_3CO_2$, $ArCO_2$, $CH_3SO_3$, p-tolyl$SO_3$, HSO4 and $H_2PO_4$.

27. The method of claim 24 wherein in the metal complex is of the formula $[RuX_2(PR^2{}_3)_n]_p$ wherein $R^2$ is an alkyl or aryl; X is a halide; n is 1, 2, 3 or 4; and p is at least 1.

28. The method of claim 24 wherein the metal complex is of the formula $[RuYX(PR^2{}_3)_n]_p$ wherein $R^2$ is an alkyl or aryl and wherein n=3, Y=H and X=Cl; or n=3, Y=H, p is at least 1 and X=H; or n=4, p is at least 1, X=H, Y=H; or n=2, 3 or 4, p is at least 1 and X=Y is selected from the group consisting of $ClO_4$, $PF_6$, $BF_4$, $CF_3CO_2$, $CF_3SO_3$, $CH_3CO_2$, $ArCO_2$, $CH_3SO_3$, p-tolyl$SO_3$, HSO4 and $H_2PO_4$.

29. An improved metal catalyst recovery method comprising:
a) catalytically converting a compound of Formula I into a compound of Formula II utilizing at least one transition metal complex of a tertiary phosphine of the formula $[M(PR^3R^4R^5)_nX_m]_p$; wherein $R^1$ is H, alkyl, aryl or acyl;

M is a Group VIII transition metal; $R^3$, $R^4$ and $R^5$ are selected from the group consisting of alkyl, aryl, alkoxyl, phenoxyl and combinations thereof; X is a halide or an anion; n is 1, 2, 3 or 4; m is 1 or 2; and p is at least 1; and

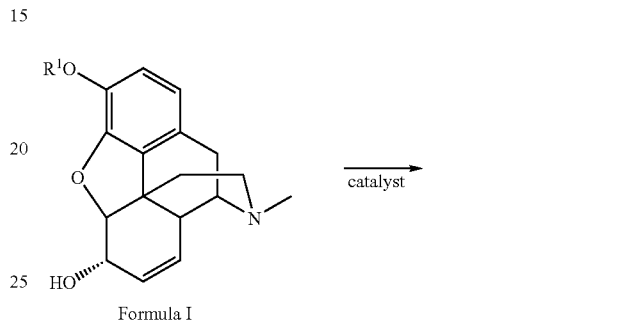

Formula I

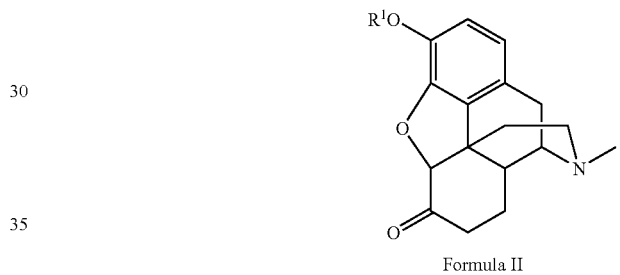

Formula II b) recovering the metal containing solid catalyst.

30. The method of claim 29 wherein $R^1$ is H or $CH_3$.

31. The method of claim 29 wherein $(PR^3R^4R^5)_n$ is supported by a solid.

32. The method of claim 29 wherein $(PR^3R^4R^5)_n$ is selected from the group consisting of polymer supported $(PR^3R^4R^5)_n$, silical supported $(PR^3R^4R^5)_n$, resin-bound $(PR^3R^4R^5)_n$ and mixtures thereof.

* * * * *